US011390578B2

(12) United States Patent
Ernst et al.

(10) Patent No.: US 11,390,578 B2
(45) Date of Patent: Jul. 19, 2022

(54) METHOD FOR SYNTHESIZING AMINES

(71) Applicant: BASF SE, Ludwigshafen am Rhein (DE)

(72) Inventors: Martin Ernst, Ludwigshafen am Rhein (DE); Ansgar Gereon Altenhoff, Ludwigshafen am Rhein (DE); Hermann Luyken, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/045,644

(22) PCT Filed: Mar. 27, 2019

(86) PCT No.: PCT/EP2019/057682
§ 371 (c)(1),
(2) Date: Oct. 6, 2020

(87) PCT Pub. No.: WO2019/192903
PCT Pub. Date: Oct. 10, 2019

(65) Prior Publication Data
US 2021/0155574 A1    May 27, 2021

(30) Foreign Application Priority Data
Apr. 6, 2018   (EP) .................................. 18165995

(51) Int. Cl.
*C07C 211/27* (2006.01)
*C07C 209/16* (2006.01)

(52) U.S. Cl.
CPC .......... *C07C 211/27* (2013.01); *C07C 209/16* (2013.01)

(58) Field of Classification Search
CPC ... C07C 211/27; C07C 209/16; C09D 163/00; C08L 63/00
See application file for complete search history.

(56) References Cited

U.S. PATENT DOCUMENTS

| | | | | |
|---|---|---|---|---|
| 4,845,296 A * | 7/1989 | Ahmed | ................. | C07C 213/04 564/477 |
| 5,294,638 A * | 3/1994 | Hell | ...................... | C07C 217/62 514/452 |
| 8,017,808 B2 * | 9/2011 | Eberhardt | ......... | C07D 295/023 564/480 |
| 8,487,135 B2 * | 7/2013 | Kubanek | ................ | B01J 37/031 564/480 |
| 8,552,078 B2 | 10/2013 | Vedage et al. | | |
| 10,221,344 B2 * | 3/2019 | Kasemi | .................... | C08K 5/07 |
| 10,287,388 B2 * | 5/2019 | Kasemi | ................ | C08G 59/223 |
| 10,301,423 B2 * | 5/2019 | Kasemi | .............. | C08G 59/5033 |
| 10,662,280 B2 * | 5/2020 | Burckhardt | ........... | C07C 217/32 |
| 10,899,926 B2 * | 1/2021 | Kasemi | ................ | C09D 163/00 |
| 2008/0255185 A1 * | 10/2008 | Moreno | ............. | A61K 31/4188 514/387 |
| 2009/0082562 A1 * | 3/2009 | Eberhardt | .......... | C07D 295/023 544/178 |
| 2011/0137030 A1 * | 6/2011 | Kubanek | ............... | C07C 213/02 544/178 |
| 2012/0232293 A1 * | 9/2012 | Schaub | ................. | C07C 213/02 549/492 |
| 2014/0046054 A1 * | 2/2014 | Wetzel | .................. | C07C 209/18 540/484 |
| 2015/0266878 A1 * | 9/2015 | Yang | ....................... | A61P 35/00 546/271.7 |
| 2016/0194436 A1 * | 7/2016 | Karl | ........................ | C07C 33/20 523/400 |
| 2019/0048127 A1 | 2/2019 | Kasemi et al. | | |
| 2020/0040215 A1 * | 2/2020 | Kasemi | ................ | C09D 163/00 |

FOREIGN PATENT DOCUMENTS

| | | | | |
|---|---|---|---|---|
| WO | WO-2007107477 A1 * | 9/2007 | ......... | C07D 295/023 |
| WO | WO-2011067199 A1 * | 6/2011 | .......... | C07D 295/03 |
| WO | WO-2012000952 A1 | 1/2012 | | |
| WO | WO-2014184039 A1 | 11/2014 | | |
| WO | WO-2016023837 A1 | 2/2016 | | |
| WO | WO-2016023839 A1 | 2/2016 | | |
| WO | WO-2017037069 A1 | 3/2017 | | |
| WO | WO-2017037070 A1 | 3/2017 | | |

OTHER PUBLICATIONS

Kirk-Othmer Encyclopedia of Chemical Technology, "Alkanolamines From Olefin Oxides and Ammonia" (2000) (Year: 2000).*
ThermoFisher Scientific, "Safety Data Sheet" (creation date Sep. 20, 2010) (Year: 2010).*
C. Yue et al., 477 Molecular Catalysis (2019) (Year: 2019).*
International Search Report for PCT/EP2019/057682 dated Jun. 17, 2019.
Written Opinion of the International Searching Authority for PCT/EP2019/057682 dated Jun. 17, 2019.
European Search Report for EP Patent Application No. 18165995.4, dated Sep. 20, 2018, 3 pages.
International Preliminary Reporton Patentability received for PCT Patent Application No. PCT/EP2019/057682, dated Oct. 15, 2020, 14 pages. (8 pages of English Translation and 6 pages of Original Document).
Kurganov, et al., "Synthesis of isomeric n-benzyl derivatives of 1,2-propanediamine", Liebigs Annalen der Chemie, vol. 1980, Issue 5, May 30, 1980, pp. 786-790.

(Continued)

*Primary Examiner* — Alexander R Pagano
(74) *Attorney, Agent, or Firm* — Faegre Drinker Biddle & Reath LLP

(57) ABSTRACT

The invention relates to a process for preparing certain amines, wherein, in a first step, a corresponding amino alcohol is reacted with a suitable carbonyl compound and then, in a second step, the intermediate obtained in the first step is reacted with a suitable amine component to form the desired amine.

17 Claims, No Drawings

(56) References Cited

OTHER PUBLICATIONS

Mokrov, et al., "Synthesis and selected properties of N-substituted pyrrolo[2,1-c]-1,3-diazacycloalkano[1,2-a]pyrazinones", Russian Chemical Bulletin, vol. 59, Issue 6, Dec. 2, 2010, pp. 1254-1266.

* cited by examiner

METHOD FOR SYNTHESIZING AMINES

CROSS-REFERENCE TO RELATED APPLICATIONS

This application is a national stage application (under 35 U.S.C. § 371) of PCT/EP2019/057682, filed Mar. 27, 2019, which claims benefit of European Application No. 18165995.4, filed Apr. 6, 2018, both of which are incorporated herein by reference in their entirety.

BACKGROUND OF THE INVENTION

The present invention relates to a process for preparing amines of the formula (1),

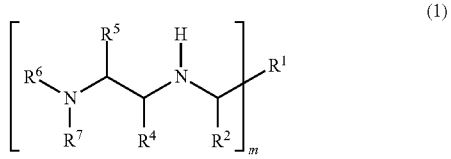

in which
m is 1, 2 or 3, wherein
when m is 1
$R^1$ is an aliphatic $C_{1-60}$ hydrocarbon radical or $C_{4-60}$ hydrocarbon radical that contains at least one cycloaliphatic or aromatic ring, said $C_{1-60}$ or $C_{4-60}$ hydrocarbon radical optionally containing one or more heteroatoms independently selected from the group consisting of nitrogen (N), oxygen (O), and sulfur (S), and
$R^2$ is hydrogen (H), $C_{1-6}$ alkyl or phenyl,
or
$R^1$, $R^2$ together are —$(CH_2)_j$—Y—$(CH_2)_k$—, where Y is methylene, oxygen (O), sulfur (S), or $NR^3$ (where $R^3$ is $C_{1-4}$ alkyl) and j and k are independently an integer from 1 to 4,
when m is 2 or 3
$R^1$ is a di- or trivalent $C_{4-20}$ hydrocarbon radical that contains at least one cycloaliphatic or aromatic ring, said hydrocarbon radical optionally containing one or more heteroatoms independently selected from the group consisting of nitrogen (N), oxygen (O), and sulfur (S), and
$R^2$ is hydrogen (H), $C_{1-6}$ alkyl or phenyl, and
$R^4$ and $R^5$ are independently hydrogen (H) or $C_{1-16}$ alkyl,
$R^6$ and $R^7$ are independently hydrogen (H) or $C_{1-4}$ alkyl.

PRIOR ART

Such amines are used inter alia as intermediates in the preparation of biologically active substances (Mokrov G. V. et al., Russian Chemical Bulletin, 59(6), 1254-1266, 210). They are also used as crosslinkers in polyurethane foams (U.S. Pat. No. 8,552,078 B2). Ways of preparing such amines are generally known.

Mokrov G. V. et al. (Mokrov G. V. et al., Russian Chemical Bulletin, 59(6), 1254-1266, 210) describe inter alia the preparation of N-benzyl-1,2-ethanediamine through the reaction of benzaldehyde with a 3-fold excess of 1,2-ethanediamine (1,2-EDA).

Kurganov A. et al. (Liebigs Ann. Chem. 1980, 786-790) describe inter alia the preparation of $N^1$-benzyl-1,2-propanediamine through the reaction of benzaldehyde with 1,2-propanediamine (1,2-PDA).

U.S. Pat. No. 8,552,078 B2 (Air Products and Chemicals, Inc.) describes the reaction of polyamines with suitable aldehydes and ketones, for example the reaction of 1,2-EDA with benzaldehyde to form N-benzyl-1,2-ethylenediamine.

WO 2016/023839 A1 (Sika Technology AG) describes the reaction of 1,2-PDA with an appropriate aldehyde or ketone (for example the reaction with benzaldehyde to form $N^1$-benzyl-1,2-propylenediamine).

WO 2017/037069 A1 (Sika Technology AG) describes the reaction of 1,2-EDA with an appropriate aldehyde or ketone (for example the reaction with benzaldehyde to form N-benzyl-1,2-ethanediamine). The principal by-product is multiply alkylated 1,2-EDA (for example N,N'-benzyl-1,2-ethylenediamine).

WO 2016/023837 A1 (Sika Technology AG) describes the reaction of 1,2-PDA with a di- or trifunctional carbonyl compound (for example the reaction with terephthalaldehyde to form 1,4-bis(2-aminopropylaminomethyl)benzene).

WO 2017/037070 A1 (Sika Technology AG) describes the reaction of 1,2-EDA with a di- or trifunctional carbonyl compound (for example the reaction with terephthalaldehyde to form 1,4-bis(2-aminoethylaminomethyl)benzene).

According to the prior art described above, an appropriately alkylated amine may be prepared by reacting 1,2-EDA or 1,2-PDA with an appropriate aldehyde or ketone. This is accompanied by the formation of undesired by-products in which both nitrogen atoms are alkylated. When 1,2-EDA/1,2-PDA is reacted with an equimolar amount of aldehyde/ketone, the selectivity is in need of improvement, as corresponding by-products are formed in not inconsiderable amounts. The formation of such by-products may be reduced by using an excess of 1,2-EDA or 1,2-PDA. However, this gives rise to the problem of having to remove the excess diamine from the reaction mixture, which is achieved primarily by distillation. In other words, although it is possible to boost the selectivity by using an excess of diamine (starting material), this is accompanied by an increase in the running costs of the process due to the energy required by the distillation.

A further problem arises in particular when relatively small amounts of a desired amine are to be produced (for example just a few tons). It is not possible for the diamine (starting material) removed by distillation to be freely recycled into the reaction. This means that, after the desired amount of the amine has been produced, disposal (for example incineration) of the diamine (starting material) removed is normally necessary. This is a considerable economic disadvantage, particularly in the case of relatively costly starting materials such as 1,2-EDA or 1,2-PDA.

It was therefore an object of the present invention to improve the economic viability of existing processes for preparing amines of the formula (1) and to address one or more disadvantages of the prior art, in particular the above-mentioned disadvantages. A process should therefore be found that allows amines of the formula (1) to be prepared with high conversion, yield, space-time yield (STY), and selectivity. Such a process should also make it possible to prepare amines of the formula (1) based on starting materials other than corresponding diamines (for example 1,2-EDA or 1,2-PDA). [Space-time yields are expressed in 'Product amount/(Catalyst volume·Time)' (kg/($l_{cat}$·h)) and/or 'Product amount/(Reactor volume·Time)' (kg/($l_{reactor}$·h))].

Surprisingly, a process for preparing amines of the formula (1)

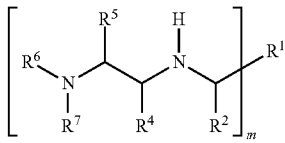
(1)

has been found in which
m is 1, 2 or 3, wherein
when m is 1
  $R^1$ is an aliphatic $C_{1-60}$ hydrocarbon radical or $C_{4-60}$ hydrocarbon radical that contains at least one cycloaliphatic or aromatic ring, said $C_{1-60}$ or $C_{4-60}$ hydrocarbon radical optionally containing one or more heteroatoms independently selected from the group consisting of nitrogen (N), oxygen (O), and sulfur (S), and
  $R^2$ is hydrogen (H), $C_{1-6}$ alkyl or phenyl,
or
  $R^1$, $R^2$ together are —$(CH_2)_j$—Y—$(CH_2)_k$—, where Y is methylene, oxygen (O), sulfur (S), or $NR^3$ (where $R^3$ is $C_{1-4}$ alkyl) and j and k are independently an integer from 1 to 4,
when m is 2 or 3
  $R^1$ is a di- or trivalent $C_{4-20}$ hydrocarbon radical that contains at least one cycloaliphatic or aromatic ring, said hydrocarbon radical optionally containing one or more heteroatoms independently selected from the group consisting of nitrogen (N), oxygen (O), and sulfur (S), and
  $R^2$ is hydrogen (H), $C_{1-6}$ alkyl or phenyl, and
$R^4$ and $R^5$ are independently hydrogen (H) or $C_{1-16}$ alkyl,
$R^6$ and $R^7$ are independently hydrogen (H) or $C_{1-4}$ alkyl,
comprising the steps of
1. reacting an amino alcohol of the formula (2)

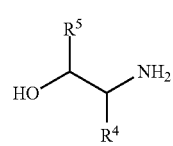
(2)

with a carbonyl compound of the formula (3)

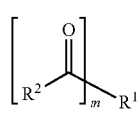
(3)

and subsequent hydrogenation of the resulting reaction product with hydrogen ($H_2$) on a heterogeneous hydrogenation catalyst to form an intermediate of the formula (4)

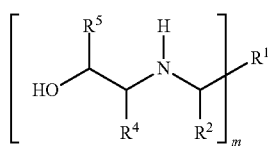
(4)

2. reacting the intermediate obtained in step 1 with an amine component of the formula (5)

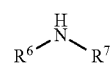
(5)

in the presence of hydrogen ($H_2$) and a heterogeneous hydrogenation catalyst to form a corresponding amine of the formula (1),
where m and the radicals $R^1$, $R^2$, $R^4$, $R^5$, $R^6$, and $R^7$ in the formulas (2) to (5) are as defined in formula (1).

It was surprisingly found that amines of the formula (1) are obtained with high yield and selectivity using the process of the invention. Those skilled in the art would in principle have expected to see losses in yield in both the first and second step, with the overall losses being greater than that of the one-step process of the prior art. The key premise for this expectation is that the second step (step 2) is an alcohol amination, which usually takes place at higher temperatures and pressures than aminations of ketones or aldehydes. The higher temperatures and pressures are necessary in order to first oxidize (dehydrogenate) the corresponding alcohol group to the aldehyde or ketone, which is then able to react with the amine component. However, increasing temperature and increasing pressure are usually accompanied by an increasing likelihood that undesirable side reactions will occur to a significant degree. In this regard, those skilled in the art would favor the amination of an aldehyde or ketone over that of an alcohol. In particular, those skilled in the art would not expect the selectivity of the prior art process (one step, amination of an aldehyde or ketone) to be lower than that of the process of the invention (two steps; step 1: amination of an aldehyde or ketone, step 2: amination of an alcohol).

DESCRIPTION OF THE INVENTION

The process of the invention can be used to prepare amines of the formula (1) with high yield and selectivity, the starting materials used being amino alcohols of the formula (2), for example 1-aminopropan-2-ol (MIPOA) or monoethanolamine (MEOA). Such starting materials can be prepared more easily and therefore more economically than the diamines used in the prior art, such as 1,2-EDA or 1,2-PDA.
Description of the Radicals $R^1$ to $R^7$:
General:
An "aliphatic radical" refers to a radical that contains neither a cycloaliphatic nor an aromatic ring. It may be linear or branched. According to the invention, the linear or branched carbon backbone may also contain corresponding heteroatoms, that is to say nitrogen (N), oxygen (O), and sulfur (S).

When m is 1, $R^1$ is a monovalent radical; when m is 2, $R^1$ is a divalent radical; when m is 3, $R^1$ is a trivalent radical. The valency of $R^1$ therefore corresponds to the value of m.

$R^1$ is preferably saturated. In the case of a hydrocarbon radical that contains at least one aromatic ring, it is understood that $R^1$ contains no CC double bonds other than those that are formally part of the aromatic ring.

When $R^1$ contains heteroatoms, these are preferably incorporated into the hydrocarbon radical in the following ways: C—O—C, C—S—C, C—N=C, C—N—CC, more preferably C—O—C, C—S—C, C—N—CC, particularly preferably C—O—C, C—N—CC, or even C—O—C(C—N—CC means that the nitrogen is bonded to all three carbon atoms).

The heteroatoms according to the invention may be part of the cycloaliphatic or aromatic ring or they may be situated outside the ring. Furyl is an example of a radical in which the heteroatom is part of the aromatic ring. Similarly, in 2,5-tetrahydrophenylene the heteroatom is part of the cycloaliphatic ring. 4-methoxybenzyl is an example of a radical in which the heteroatom is outside the aromatic ring. In all cases, the oxygen forms part of the carbon backbone in a C—O—C unit.

An alkoxyalkyl radical is an example of an aliphatic radical that contains a corresponding heteroatom (oxygen (O)).

A dashed line in the formulae according to the invention in each case represents the bond between the radical $R^1$ and the associated molecular radical (i.e. the molecular fragment shown in square brackets in the formulas (1), (3) and (4)).

m may be 1, 2 or 3. Preferably, m is 1 or 2, particularly preferably 1.

Preparation of Amines in which m is 1:

The process of the invention is hereinbelow described in more detail first with regard to the preparation of amines in which m is 1. Preference here is given to preparing amines in which the radicals $R^1$ to $R^7$ are as defined below.

The process of the invention is particularly suitable for preparing amines of the formula (1) in which m is 1 and where the chosen radicals $R^1$, $R^2$, $R^6$, and $R^7$ are not such that the group $R^6R^7N$— corresponds to the group —NHCHR$^1$R$^2$. For example, $R^6$ should not be ethyl and $R^7$ hydrogen (FI) at the same time as $R^1$ being methyl and $R^2$ hydrogen (FI).

$R^1$ and $R^2$:

$R^1$ is preferably an aliphatic $C_{6-60}$ hydrocarbon radical, more preferably a $C_{6-40}$ hydrocarbon radical, and particularly preferably a $C_{7-30}$, or even $C_{8-20}$ hydrocarbon radical.

$R^1$ is likewise preferably a $C_{4-60}$ hydrocarbon radical, more preferably a $C_{5-50}$ hydrocarbon radical, and particularly preferably a $C_{6-40}$ hydrocarbon radical, or even $C_{7-30}$ hydrocarbon radical, said radical containing at least one cycloaliphatic or aromatic ring.

$R^1$ may for example be
- $C_{3-60}$ alkyl (preferably $C_{4-40}$ alkyl, more preferably $C_{6-30}$ alkyl, particularly preferably $C_{6-20}$ alkyl),
- $C_{3-50}$ alkoxyalkyl (preferably $C_{4-40}$ alkoxyalkyl, more preferably $C_{5-30}$ alkoxyalkyl, particularly preferably $C_{6-20}$ alkoxyalkyl),
- $C_{4-12}$ cycloalkyl (preferably $C_{4-10}$ cycloalkyl, more preferably $C_{5-8}$ cycloalkyl, particularly preferably cyclohexyl),
- $C_{4-30}$ alkoxycycloalkyl (preferably $C_{6-20}$ alkoxycycloalkyl, more preferably $C_{7-15}$ alkoxycycloalkyl, particularly preferably $C_{8-12}$ alkoxycycloalkyl),
- $C_{4-30}$ alkylcycloalkyl (preferably $C_{6-20}$ alkylcycloalkyl, more preferably $C_{7-15}$ alkylcycloalkyl, particularly preferably $C_{8-12}$ alkylcycloalkyl), or radicals of the formula (A), (B), or (C),

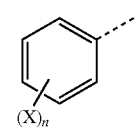
(A)

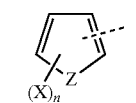
(B)

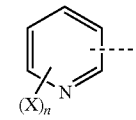
(C)

where, in formulas (A), (B), and (C)
- X are identical or different radicals selected from the group consisting of $C_{1-18}$ alkyl, $C_{1-18}$ alkoxy, and $C_{1-18}$ dialkylamino, preferably $C_{1-12}$ alkyl, $C_{1-12}$ alkoxy, and $C_{1-12}$ dialkylamino, more preferably $C_{1-4}$ alkyl, $C_{1-4}$ alkoxy, and $C_{1-4}$ dialkylamino, particularly preferably methyl, methoxy or dimethylamino,
- Z is oxygen (O), sulfur (S), or $NR^9$ (where $R^9$ is $C_{1-4}$ alkyl, preferably methyl or ethyl, particularly preferably methyl), preferably oxygen (O) or sulfur (S), more preferably oxygen (O),
- n is an integer from 0 to 3, preferably 0 or 1 or 2, more preferably 0 or 1.

An alkoxycycloalkyl or an alkylcycloalkyl in the context of the present invention is to be understood as meaning a cycloalkyl radical that has at least one alkoxy or alkyl group.

$R^1$ is particularly preferably a radical of the formula (A) in which X, Z, and n are each as defined above.

When $R^1$ is as defined above, then $R^2$ is preferably hydrogen (H), methyl, ethyl or phenyl.

The carbonyl compound used may also be a cyclic ketone (for example cyclohexanone). In such cases, $R^1$ and $R^2$ together form a corresponding ring. In this case, $R^1$, $R^2$ together are preferably —(CH$_2$)$_j$—Y—(CH$_2$)$_k$—, where
- Y is methylene, oxygen (O), sulfur (S), or $NR^3$ (where $R^3$ is $C_{1-4}$ alkyl, preferably methyl or ethyl, more preferably methyl), preferably methylene, oxygen (O), or sulfur (S), more preferably methylene or oxygen (O), particularly preferably methylene, and
- j and k are independently an integer from 1 to 4, preferably 1 to 2, more preferably both 2.

$R^2$ is in particular hydrogen (H), methyl, ethyl or phenyl, more preferably hydrogen (H), methyl or phenyl, particularly preferably hydrogen (H) or methyl, or even exclusively hydrogen (H).

The following aldehydes and ketones are preferably used as the carbonyl compound:

Aldehydes:
Benzaldehyde, 2-methylbenzaldehyde (o-tolualdehyde), 3-methylbenzaldehyde (m-tolualdehyde), 4-methylbenzaldehyde (p-tolualdehyde), 2,5-dimethylbenzaldehyde, 4-ethylbenzaldehyde, 4-isopropylbenzaldehyde (cuminaldehyde), 4-tert-butylbenzaldehyde, 2-methoxybenzaldehyde (o-anisaldehyde), 3-methoxybenzaldehyde (m-anisaldehyde), 4-methoxybenzaldehyde (anisaldehyde), 2,3-dimethoxybenzaldehyde, 2,4-dimethoxybenzaldehyde, 2,5-dimethoxybenzaldehyde, 3,4-dimethoxybenzaldehyde (veratrumaldehyde), 3,5-dimethoxybenzaldehyde, 2,4,6-trimethylbenzaldehyde, 2,4,5-trimethoxybenzaldehyde (asaronaldehyde), 2,4, 6-trimethoxybenzaldehyde, 3,4,5-trimethoxybenzaldehyde, 4-dimethylaminobenzaldehyde, furan-2-aldehyde, furan-3-aldehyde.

Ketones:

Methyl isoamyl ketone, 3-octanone, acetone, acetophenone, benzophenone, 2'-methylacetophenone, 3'-methylacetophenone, 4'-methylacetophenone, 2'-methoxyacetophenone, 3'-methoxyacetophenone, 4'-methoxyacetophenone, 2',4'-dimethylacetophenone, 2',5'-dimethylacetophenone, 3',4'-dimethylacetophenone, 3',5'-dimethylacetophenone, 2',4'-dimethoxyacetophenone, 2',5'-dimethoxyacetophenone, 3',4'-dimethoxyacetophenone, 3',5'-dimethoxyacetophenone, 2',4',6'-trimethylacetophenone, 2',4',6'-trimethoxyacetophenone or cyclohexanone.

It is accordingly preferable that $R^1$ and $R^2$ are both methyl or both phenyl, $R^1$ is 3-methylbutyl and $R^2$ methyl, or $R^1$ is n-pentyl and $R^2$ ethyl, or $R^1$ is selected from the group consisting of i-propyl, phenyl, 2-methylphenyl, 3-methylphenyl, 4-methylphenyl, 2,5-dimethylphenyl, 4-ethyl phenyl, 4-isopropylphenyl, 4-tert-butylphenyl, 2-methoxyphenyl, 3-methoxyphenyl, 4-methoxyphenyl, 2,3-dimethoxyphenyl, 2,4-dimethoxyphenyl, 2,5-dimethoxyphenyl, 3,4-dimethoxyphenyl, 3,5-dimethoxyphenyl, 2,4,5-trimethylphenyl, 2,4,6-trimethylphenyl, 2,4,5-trimethoxyphenyl, 2,4,6-trimethoxyphenyl, 3,4,5-trimethoxyphenyl, 2-dimethylaminophenyl, 3-dimethylaminophenyl, 4-dimethylaminophenyl, 2-furyl, and 3-furyl, and $R^2$ is hydrogen (H) or methyl;

or $R^1$ and $R^2$ are together n-pentylene.

It is more preferable that $R^1$ and $R^2$ are both phenyl or $R^1$ is selected from the group consisting of phenyl, 4-isopropylphenyl, 4-tert-butylphenyl, 4-methoxyphenyl, 4-dimethylaminophenyl, 2-furyl, and 3-furyl, $R^2$ is hydrogen (H), or $R^1$ is selected from the group consisting of phenyl, 4-methylphenyl, 4-methoxyphenyl, $R^2$ is methyl.

Particularly preferably $R^1$ is phenyl and $R^2$ hydrogen (H).

Unless explicitly stated otherwise, what is stated below for the radicals $R^4$, $R^5$, $R^6$, and $R^7$ applies both to amines of the formula (1) in which m is 1 and to those in which m is 2 or 3.

$R^4$ and $R^5$:

$R^4$ and $R^5$ are preferably independently hydrogen (H) or $C_{1-10}$ alkyl, more preferably hydrogen (H) or $C_{1-4}$ alkyl, in particular methyl. Particular preference is given in particular to using MEOA or 1-aminopropan-2-ol (MIPOA) or its structural isomer 2-aminopropan-1-ol (MIPOA') as the amino alcohol. It is accordingly very particularly preferable when $R^4$ or $R^5$ is methyl and the other radical in each case is hydrogen (H) or $R^4$ and $R^5$ are both hydrogen (H).

The MEOA used may be obtained from the reaction of ethylene oxide (EO) with ammonia. MIPOA may be produced by reacting propylene oxide (PO) with ammonia. Since these are efficient and therefore inexpensive routes of production, it is preferable that the MEOA and MIPOA used according to the invention are produced by reacting EO with ammonia or PO with ammonia. The MIPOA thus produced usually contains small amounts of MIPOA'. It is preferable that MIPOA and MIPOA' are not separated from one another, but that a mixture of MIPOA and MIPOA' is reacted in step 1. MIPOA and MIPOA' are obtained from the reaction of PO with ammonia in a molar ratio of 15:1 to 23:1, preferably 16:1 to 22:1, more preferably 17:1 to 21:1, particularly preferably 18:1 to 20:1. MIPOA and MIPOA' are accordingly usually used in an appropriate molar ratio, i.e. 15:1 to 23:1, preferably 16:1 to 22:1, more preferably 17:1 to 21:1, particularly preferably 18:1 to 20:1.

When, for m=1 in step 1, such a mixture of MIPOA and MIPOA' is reacted with a carbonyl compound of the formula (3), this results in two different intermediates. For the intermediate resulting from MIPOA, $R^4$=H and $R^5$=methyl. For the intermediate resulting from MIPOA', $R^4$=methyl and $R^5$=H. When these two intermediates are reacted with an amine of the formula (5) according to step 2, two different amines of the formula (1) are obtained. In turn, for the amine resulting from MIPOA, $R^4$=H and $R^5$=methyl and, for the amine resulting from MIPOA', $R^4$=methyl and $R^5$=H. The molar ratio in which the two amines of the formula (1) are formed depends here on the molar ratio of MIPOA to MIPOA'.

With the process of the invention, preference is therefore given in particular to preparing amines of the formula (1) in which m is 1 and in which $R^4$ is hydrogen (H) and $R^5$ is methyl (formula (1.1)) or $R^4$ is methyl and $R^5$ is hydrogen (H) (formula (1.2)),

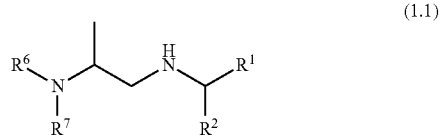

(1.1)

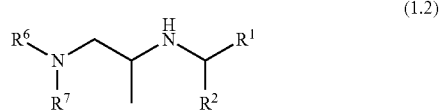

(1.2)

where in step 1, 1-aminopropan-2-ol (MIPOA) and 2-aminopropan-1-ol (MIPOA') are reacted with a carbonyl compound of the formula (3) to form the respective intermediates of the formulas (4.1) and (4.2),

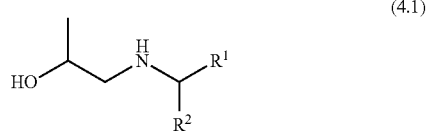

(4.1)

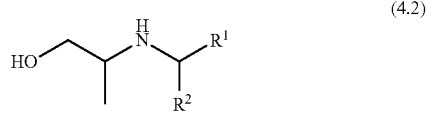

(4.2)

in step 2, the intermediates obtained in step 1 are reacted with an amine component of the formula (5) to form the corresponding amines of the formulas (1.1) and (1.2).

The amines of the formula (1.1) and formula (1.2) are thus prepared at the same time (i.e. side by side). The molar ratio of the amines of the formula (1.1) and formula (1.2) thus obtained is essentially determined by the molar ratio of MIPOA to MIPOA'. Experimentally, it is found that the molar ratio of amine of formula (1.1) to amine of formula (1.2) is smaller than the molar ratio of MIPOA to MIPOA'. It is assumed that a mixture of MIPOA and MIPOA' (19:1 molar ratio) is reacted with benzaldehyde in step 1 and the resulting intermediates are then reacted with ammonia in step 2. This results in a mixture of $N^1$-benzyl-1,2-propanediamine and $N^2$-benzyl-1,2-propanediamine. Secondary alcohols usually react more rapidly than primary alcohols with respect to the respective amine. Depending on the reaction conditions, the molar ratio of $N^1$-benzyl-1,2-propanediamine to $N^2$-benzyl-1,2-propanediamine may therefore be greater than that of MIPOA to MIPOA'.

$R^6$ and $R^7$:

$R^6$ and $R^7$ are preferably independently hydrogen (H) or $C_{1-2}$ alkyl. Particular preference is given in particular to using dimethylamine (DMA), methylamine or ammonia. It is accordingly more preferable when $R^6$ and $R^7$ are both methyl or both hydrogen (H), or when $R^6$ or $R^7$ are methyl and the other radical is in each case hydrogen (H). Particular preference is given to using ammonia. It is accordingly particularly preferable when $R^6$ and $R^7$ are hydrogen (H).

The process of the invention may preferably be used to prepare amines of the formula (1) in which m is 1, where
  $R^1$ and $R^2$ are both methyl or both phenyl, $R^1$ is 3-methylbutyl and $R^2$ methyl, or $R^1$ is n-pentyl and $R^2$ ethyl,
  or
  $R^1$ is selected from the group consisting of i-propyl, phenyl, 2-methylphenyl, 3-methylphenyl, 4-methylphenyl, 2,5-dimethylphenyl, 4-ethylphenyl, 4-isopropylphenyl, 4-tert-butylphenyl, 2-methoxyphenyl, 3-methoxyphenyl, 4-methoxyphenyl, 2,3-dimethoxyphenyl, 2,4-dimethoxyphenyl, 2,5-dimethoxyphenyl, 3,4-dimethoxyphenyl, 3,5-dimethoxyphenyl, 2,4,5-trimethylphenyl, 2,4,6-trimethylphenyl, 2,4,5-trimethoxyphenyl, 2,4,6-trimethoxyphenyl, 3,4,5-trimethoxyphenyl, 2-dimethylaminophenyl, 3-dimethylaminophenyl, 4-dimethylaminophenyl, 2-furyl, and 3-furyl, and
  $R^2$ is hydrogen (H) or methyl;
  or
  $R^1$ and $R^2$ are together n-pentylene,
  $R^4$ or $R^5$ are methyl and the other radical is in each case hydrogen (H) or both are hydrogen (H),
  $R^6$ and $R^7$ are hydrogen (H).

The process of the invention may particularly preferably be used to prepare amines of the formula (1) in which m is 1, where
  $R^1$ and $R^2$ are both phenyl
  or
  $R^1$ is selected from the group consisting of phenyl, 4-isopropylphenyl, 4-tert-butylphenyl, 4-methoxyphenyl, 4-dimethylaminophenyl, 2-furyl, and 3-furyl,
  $R^2$ is hydrogen (H),
  or
  $R^1$ is selected from the group consisting of phenyl, 4-methylphenyl, 4-methoxyphenyl,
  $R^2$ is methyl,
  $R^4$ or $R^5$ are methyl and the other radical is in each case hydrogen (H) or both are hydrogen (H),
  $R^6$ and $R^7$ are hydrogen (H).

The process of the invention may likewise particularly preferably be used to prepare amines of the formula (1) in which m is 1, where
  $R^1$ and $R^2$ are both phenyl
  or
  $R^1$ is selected from the group consisting of phenyl, 4-isopropylphenyl, 4-tert-butylphenyl, 4-methoxyphenyl, 4-dimethylaminophenyl, 2-furyl, and 3-furyl,
  $R^2$ is hydrogen (H),
  or
  $R^1$ is selected from the group consisting of phenyl, 4-methylphenyl, 4-methoxyphenyl,
  $R^2$ is methyl,
  $R^4$ or $R^5$ are methyl and the other radical is in each case hydrogen (H).
  $R^6$ and $R^7$ are hydrogen (H).

Very particular preference is given to preparing $N^1$-benzyl-1,2-propylenediamine and $N^2$-benzyl-1,2-propylenediamine wherein 1-aminopropan-2-ol (MIPOA) and 2-aminopropan-1-ol (MIPOA') are reacted with benzaldehyde in step 1 and the resulting intermediates (N-benzyl-1-aminopropan-2-ol and N-benzyl-2-aminopropan-1-ol) reacted with ammonia in step 2.

Likewise very particular preference is given to preparing N-benzyl-ethylenediamine wherein 2-aminoethanol is reacted with benzaldehyde in step 1 and the resulting intermediate (N-benzyl-2-aminoethanol) reacted with ammonia in step 2.

Preparation of Amines in which m is 2 or 3

The carbonyl compounds used are corresponding dialdehydes and diketones (m=2) or trialdehydes and triketones (m=3). In addition, however, ketoaldehydes (for example 2-acetylbenzaldehyde, 3-acetylbenzaldehyde or 4-acetylbenzaldehyde) may also be used.

$R^1$ is preferably a di- or trivalent $C_{4-20}$ hydrocarbon radical, more preferably a $C_{5-16}$ hydrocarbon radical, particularly preferably a $C_{6-14}$ hydrocarbon radical.

When m is 3, $R^1$ may be defined as follows:

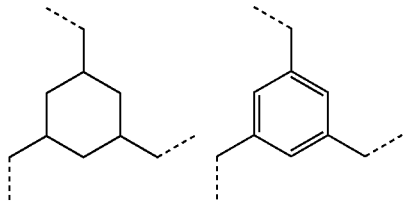

$R^2$ here is preferably hydrogen (H) or methyl.

m is preferably 2. The radicals described below therefore relate to the preparation of amines of the formula (1) in which m is 2.

$R^1$ is preferably an optionally substituted phenylene, cyclohexylene, dicycloheptylene, tricyclododecylene, pentacyclopentadecylene, furandiyl, tetrahydrofurandiyl, thiophenediyl, tetrahydrothiophenediyl, or N,N'-piperazine-bis(2,2-dimethylpropane)diyl radical.

$R^1$ is particularly preferably a phenylene radical of the formula (D)

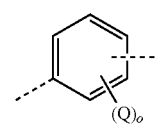

(D)

where
o is 0 or 1 or 2, and
Q are identical or different radicals selected from the group consisting of alkyl and alkoxy having in each case 1 to 4 carbon atoms.

$R^1$ is further particularly preferably a cyclohexylene radical of the formula (E), where o and Q are as defined above.

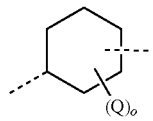

(E)

$R^1$ is further particularly preferably a furan radical or thiophene radical of the formula (F), where Z is oxygen (O) or sulfur (S).

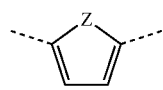

(F)

$R^1$ is further particularly preferably a tetrahydrofuran radical or tetrahydrothiophene radical of the formula (G), where Z is as defined above.

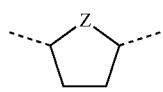

(G)

Preferably, $R^1$ is in particular selected from the group consisting of 1,2-phenylene, 1,3-phenylene, 1,4-phenylene, 1,2-cyclohexylene, 1,3-cyclohexylene, 1,4-cyclohexylene, 2(3),5(6)bicyclo[2.2.1]heptylene, 3(4),8(9)-tricyclo[5.2.1.0²,⁶]decylene, 4(5),11(12)-pentacyclo[6.5.1.1³,⁶.0²,⁷.0⁹,¹³]pentadecylene, 6,12-pentacyclo[9.2.1.1⁵,⁸.0⁴,⁹.0²,¹⁰]pentadecylene, N,N'-bis(2,2-dimethyl-1,3-propylene)piperazine, 2,5-furylene, 2,5-thiophenylene, 2,5-tetrahydrophenylene, more preferably from the group consisting of 1,2-phenylene, 1,3-phenylene, 1,4-phenylene, 1,2-cyclohexylene, 1,3-cyclohexylene, 1,4-cyclohexylene.

$R^2$ is here preferably hydrogen (H) or methyl.

The process of the invention may preferably be used to prepare amines of the formula (1) in which m is 2, where $R^1$ is selected from the group consisting of 1,2-phenylene, 1,3-phenylene, 1,4-phenylene, 1,2-cyclohexylene, 1,3-cyclohexylene, 1,4-cyclohexylene, 2(3),5(6)-bicyclo[2.2.1]heptylene, 3(4),8(9)-tricyclo[5.2.1.02,6]decylene, 4(5),11(12)-pentacyclo[6.5.1.1³,⁶.0²,⁷.0⁹,¹³]pentadecylene, 6,12-pentacyclo[9.2.1.1⁵,⁸.0⁴,⁹.0²,¹⁰]pentadecylene, N,N'-bis(2,2-dimethyl-1,3-propylene)piperazine, 2,5-furylene, 2,5-thiophenylene, 2,5-tetrahydro phenylene, $R^2$ is hydrogen (H), or $R^1$ is selected from the group consisting of 1,2-phenylene, 1,3-phenylene, 1,4-phenylene, 1,2-cyclohexylene, 1,3-cyclohexylene, 1,4-cyclohexylene, $R^2$ is methyl.

$R^4$ or $R^5$ are methyl and the other radical is in each case hydrogen (H).

$R^6$ and $R^7$ are hydrogen (H).

Catalyst:

The following description concerning possible catalysts relates to the preparation according to the invention of all possible amines of the formula (1). Unless otherwise stated, the following explanations therefore relate both to amines in which m is 1 and to those in which m is 2 or 3.

The heterogeneous hydrogenation catalyst used in the process of the invention may also be referred to hereinbelow as "catalyst".

In the process of the invention, the heterogeneous hydrogenation catalyst used in steps 1 and 2 is preferably a catalyst comprising one or more metals from group VIIIB and/or group IB of the periodic table of the elements.

Examples of such elements are Cu, Co, Ni, and/or Fe, and also noble metals such as Ru, Pt, Pd, and Re. The catalysts may be doped, for example with Ag, Zn, In, Mn, alkali metals (Li, Na, K, Rb, Cs) and/or Mo.

The designation of the groups in the periodic table of the elements is in accordance with the CAS (Chemical Abstracts Service) nomenclature.

Preferred metals of group VIIIB of the periodic table of the elements of the elements are Fe, Co, Ni, Ru, Rh, Pd, Os, Ir, Pt. Preferred elements of group IB of the periodic table of the elements are Cu, Ag, and Au.

The catalyst preferably has a support material. The support materials used are in particular aluminum oxide (gamma, delta, theta, alpha, kappa, chi or mixtures thereof), silicon dioxide, zirconium dioxide (preferably monoclinic, tetragonal or cubic modification), zeolites, aluminosilicates, and mixtures of said supports or activated carbon. Particular preference is given to zirconium dioxide and/or aluminum oxide and very particular preference is given to aluminum oxide, in particular gamma-aluminum oxide.

The catalyst used in the process of the invention comprises preferably Cu and/or Ni and/or Co, preferably Cu and Ni and/or Co, more preferably Cu and Ni and Co.

In addition, the catalyst used may also comprise Cu and/or Ni and/or Co and/or Ru, preferably Cu, Ni, Co, and Ru.

In the process of the invention, the catalysts are used preferably in the form of catalysts consisting only of catalytically active mass and optionally a shaping auxiliary (such as graphite or stearic acid) when the catalyst is used in the form of shaped bodies, i.e. not containing any other catalytically active substances.

In this context, the support material, thus aluminum oxide ($Al_2O_3$), zirconium dioxide ($ZrO_2$) in particular, is considered to be part of the catalytically active mass.

The catalysts are used in such a way that the catalytically active mass, milled into a powder, is introduced into the reaction vessel or that the catalytically active mass, after milling, mixing with shaping auxiliaries, shaping, and heat treatment, is placed in the reactor in the form of shaped catalyst bodies, for example as tablets, beads, rings, extrudates (e.g. strands).

The stated concentrations (in % by weight) of the components of the catalyst are in each case based—unless otherwise indicated—on the catalytically active mass of the finished catalyst after the last heat treatment thereof and prior to the reduction thereof with hydrogen.

In the process of the invention, preference is accordingly given to using a supported catalyst comprising copper and nickel, more preferably a supported catalyst comprising copper, nickel, and cobalt.

Very particular preference is given to using a supported catalyst comprising copper, nickel, cobalt in which the catalytically active mass of the catalyst, prior to the reduction thereof with hydrogen, comprises oxygen-containing compounds of aluminum, copper, nickel, and cobalt and from 0.2% to 0.5% by weight, preferably from 0.6% to 3.0% by weight, or even from 0.7% to 2.5% by weight, of oxygen-containing compounds of tin, calculated as SnO.

Very particular preference is likewise given to using a supported catalyst comprising copper and nickel in which the catalytically active mass of the catalyst, prior to the reduction thereof with hydrogen, comprises oxygen-containing compounds of zirconium, copper, and nickel and from 0% to 5% by weight, preferably from 0.1% to 3% by weight, of oxygen-containing compounds of molybdenum, calculated as $MoO_3$.

The catalytically active mass of the catalyst, after the last heat treatment thereof and prior to the reduction thereof with hydrogen, is defined as the sum of the masses of the catalytically active constituents and of the abovementioned catalyst support materials and preferably comprises essentially the following constituents: support material (thus preferably aluminum oxide ($Al_2O_3$) and/or zirconium dioxide ($ZrO_2$)) and oxygen-containing compounds of copper and/or nickel and/or cobalt and optionally of tin or molybdenum.

The sum of the abovementioned constituents of the catalytically active mass is typically 70% to 100% by weight, preferably 80% to 100% by weight, more preferably 90% to 100% by weight, particularly >95% by weight, very particularly >98% by weight, especially >99% by weight, for example particular preferably 100% by weight.

The catalytically active mass of the catalysts according to the invention and of those used in the process of the invention may further comprise one or more elements (oxidation state 0) or inorganic or organic compounds thereof, selected from groups IA to VIA and IB to VIIB and VIIIB of the periodic table.

Examples of such elements and compounds thereof include:
transition metals, such as Mn or $MnO_2$, Mo or $MoO_3$, W or tungsten oxides, Ta or tantalum oxides, Nb or niobium oxides or niobium oxalate, V or vanadium oxides or vanadyl pyrophosphate; lanthanides, such as Ce or $CeO_2$ or Pr or $Pr_2O_3$; alkaline earth metal oxides, such as SrO; alkaline earth metal carbonates, such as $MgCO_3$, $CaCO_3$, and $BaCO_3$; alkali metal oxides, such as $Na_2O$, $K_2O$; alkali metal carbonates, such as $Li_2CO_3$, $Na_2CO_3$, and $K_2CO_3$; boron oxide ($B_2O_3$).

The catalytically active mass of the catalyst used in the process of the invention preferably does not contain any rhenium, any ruthenium, any iron, and/or any zinc, in each case either in metallic form (oxidation state=0) or in an ionic (oxidation state≠0), especially oxidized, form.

The catalytically active mass of the catalyst used in the process of the invention preferably does not contain any silver and/or any molybdenum, in each case either in metallic form (oxidation state=0) or in an ionic (oxidation state≠0), especially oxidized, form.

The catalysts may be produced by known processes, for example by precipitation, deposition, impregnation.

Preferred catalysts contain in their catalytically active mass prior to treatment with hydrogen
20% to 85% by weight, preferably 20% to 65% by weight, more preferably 22% to 40% by weight, of oxygen-containing compounds of zirconium, calculated as $ZrO_2$,
1% to 30% by weight, particularly preferably 2% to 25% by weight, of oxygen-containing compounds of copper, calculated as CuO,
14% to 70% by weight, preferably 15% to 50% by weight, more preferably 21% to 45% by weight, of oxygen-containing compounds of nickel, calculated as NiO, the molar ratio of nickel to copper being preferably greater than 1, in particular greater than 1.2, very particularly from 1.8 to 8.5, and
0% to 5% by weight, in particular 0.1% to 3% by weight, of oxygen-containing compounds of molybdenum, calculated as $MoO_3$.

In a further variant, these preferred catalysts additionally contain in their catalytically active mass prior to treatment with hydrogen
15% to 50% by weight, in particular 21% to 45% by weight, of oxygen-containing compounds of cobalt, calculated as CoO.

The oxygen-containing compounds of copper, nickel, and optionally cobalt, respectively calculated as CuO, NiO, and CoO, in the preferred catalysts are generally present in the catalytically active mass (prior to treatment with hydrogen) in a total content of 15% to 80% by weight, preferably 35% to 80% by weight, more preferably 60% to 78% by weight, the molar ratio of nickel to copper being particularly preferably greater than 1.

Particularly preferred catalysts contain in their catalytically active mass prior to treatment with hydrogen
20% to 90% by weight, preferably 40% to 85% by weight, more preferably 60% to 80% by weight, of oxygen-containing compounds of aluminum, calculated as $Al_2O_3$,
1% to 30% by weight, preferably 2% to 25% by weight, more preferably 3% to 20% by weight, of oxygen-containing compounds of copper, calculated as CuO,
1% to 40% by weight, preferably 3% to 30% by weight, more preferably 5% to 20% by weight, of oxygen-containing compounds of nickel, calculated as NiO, the molar ratio of nickel to copper being particularly preferably greater than 1, preferably greater than 1.2, more preferably 1.8 to 8.5, and
1% to 40% by weight, preferably 3% to 30% by weight, more preferably 5% to 20% by weight, of oxygen-containing compounds of cobalt, calculated as CoO.

The oxygen-containing compounds of nickel, cobalt, and copper, respectively calculated as NiO, CoO, and CuO, are preferably present in the catalytically active mass (prior to treatment with hydrogen) in a total content of 10% to 80% by weight, more preferably 15% to 60% by weight, particularly preferably 20% to 40% by weight, the molar ratio of nickel to copper being particularly preferably greater than 1.

The production of the catalysts described above is described by way of example in WO 2012/000952 A1 (BASF SE), and WO 2014/184039 A1 (BASF SE).

Very particularly preferred catalysts contain in their catalytically active mass prior to treatment with hydrogen
15% to 80% by weight, preferably 30% to 70% by weight, more preferably 35% to 65% by weight, of oxygen-containing compounds of aluminum, calculated as $Al_2O_3$,
1% to 20% by weight, preferably 2% to 18% by weight, more preferably 5% to 15% by weight, of oxygen-containing compounds of copper, calculated as CuO,
5% to 35% by weight, preferably 10% to 30% by weight, more preferably 12% to 28% by weight, particularly preferably 15% to 25% by weight, of oxygen-containing compounds of nickel, calculated as NiO,
5.0% to 35% by weight, preferably 10% to 30% by weight, more preferably 12% to 28% by weight, particularly preferably 15% to 25% by weight, of oxygen-containing compounds of cobalt, calculated as CoO, and
0.2% to 5.0% by weight, preferably 0.4% to 4.0% by weight, more preferably 0.6% to 3.0% by weight, particularly preferably 0.7% to 2.5% by weight, of oxygen-containing compounds of tin, calculated as SnO, The molar ratio of nickel to copper is preferably greater than 1, more preferably greater than 1.2, particularly preferably within the range from 1.8 to 8.5.

The production of very particularly preferred catalysts of this kind is described by way of example in WO 2011/067199 A1.

The catalysts described above may be used both in step 1 and in step 2. The catalysts used in steps 1 and 2 may respectively be the same or they may be different.

It is also possible that
in step 1
a heterogeneous hydrogenation catalyst that is an eggshell catalyst is used, which comprises at least one metal from group VIIIB of the periodic table of the elements as the hydrogenation metal and additionally a promoter on an oxidic support, at least 80% of the metal from group VIIIB of the periodic table of the elements being present in a layer between the surface of the catalyst and a penetration depth corresponding to not more than 80% of the radius of the catalyst, calculated from the surface of the catalyst,
or
a heterogeneous hydrogenation catalyst that is a supported catalyst is used, which comprises Pd and/or Pt as the catalytically active metal and activated carbon or aluminum oxide as support, and
in step 2
a catalyst that comprises Cu and/or Ni and/or Co is used.

In step 2 it is possible to use any of the catalysts comprising Cu and/or Ni and/or Co that are identified above as preferred, more preferred, and particularly preferred.

The eggshell catalyst and the supported Pd/Pt catalyst are described in more detail hereinbelow. Step 1 may be carried out using any of the catalysts identified in the further course of the text as preferred, more preferred, and particularly preferred.

Eggshell Catalyst:

The metal of group VIIIB of the periodic table of the elements is preferably present in the defined shell in an essentially homogeneous dispersion.

The promoter is preferably present in an essentially homogeneous dispersion throughout the cross section of the catalyst.

In a preferred embodiment, the catalyst has a diameter within the range from 1.5 to 10 mm, with at least 80% of the metal of group VIIIB of the periodic table of the elements being present in a layer between the surface of the catalyst and a penetration depth of not more than 1000 µm, calculated from the surface of the catalyst.

In a catalyst of this kind, the metal of group VIIIB of the periodic table of the elements forms a shell structure in the catalyst.

The catalyst employable according to the invention preferably has a diameter within the range from 1.5 to 9 mm. In particularly preferred embodiments, the diameter of the catalysts employable according to the invention is 2.0 to 5 mm, in particular 2.5 to 3.5 mm.

In the catalyst employable according to the invention, preferably at least 80%, more preferably at least 90%, particularly preferably at least 95%, in particular at least 98%, specifically 100%, of the metal of group VIIIB of the periodic table of the elements is present in a layer between the surface of the catalyst and a penetration depth of not more than 1000 µm, calculated from the surface of the catalyst.

The catalyst employable according to the invention comprises a metal of group VIIIB of the periodic table of the elements (Fe, Ru, Os, Co, Rh, Ir, Ni, Pd, Pt). In a preferred embodiment of the present invention, this metal is palladium.

The catalyst employable according to the invention additionally comprises at least one promoter. This may, for example, be other metals of groups VIIIB, IB, and IIB of the periodic table of the elements (Cu, Ag, Au, Zn, Cd, Hg). In a preferred embodiment, the catalysts employable according to the invention comprise, in addition to the metal of group VIIIB of the periodic table of the elements, at least one metal from group IB of the periodic table of the elements. Particular preference is given here to silver.

In a particularly preferred embodiment, the catalyst employable according to the invention comprises palladium and silver.

The catalyst employable according to the invention may be of any desired shape, for example extrudates, hollow extrudates, tablets, rings, spherical particles or spheres. Preference is given to catalysts in the form of an extrudate.

The metals may be in pure metallic form or they may be in the form of compounds, for example in the form of metal oxides. Under the operating conditions of step 2, they are generally in the form of metals. Any oxides may be converted into metals in a manner known to those skilled in the art prior to using the catalyst in a hydrogenation process; this may be done inside or outside a hydrogenation reactor, for example by prior reduction and—if necessary or advantageous for manipulations with the prereduced catalyst—subsequent surface passivation.

The content in the catalyst of metal(s) of group VIIIB of the periodic table, in particular palladium, is preferably not less than 0.01% by weight, more preferably not less than 0.1% by weight, in particular not less than 0.15% by weight. This content is preferably not more than 5% by weight, more preferably not more than 1% by weight, in particular not more than 0.6% by weight. Although lower and higher contents are possible, they are usually economically unsatisfactory on account of activity being too low or raw material costs too high. In a particularly preferred embodiment, only one hydrogenation metal, in particular palladium, is used.

The ratio of the amounts of hydrogenation metal of group VIIIB of the periodic table of the elements and additives or dopants is a parameter to be optimized in each individual case. The ratio of atoms of metal of group VIIIB of the periodic table of the elements, particularly preferably palladium, to the promoter, particularly preferably silver, is preferably 0.1-10, more preferably 2-7, in particular 2.5-6.

The oxidic support of the catalyst employable according to the invention is preferably aluminum oxide, more preferably in a mixture of δ-, θ-, and α-aluminum oxide. In addition to unavoidable impurities, the support may also comprise other additives to a certain extent. For example, it may comprise other inorganic oxides such as oxides of metals of groups IIA, IIIB, IVB, IIIA, and IVA of the periodic table of the elements, in particular silicon dioxide, titanium dioxide, zirconium dioxide, zinc oxide, magnesium oxide, sodium oxide, and/or calcium oxide. The maximum content in the support of such oxides other than aluminum oxide depends on the oxide actually present, but can be determined in the individual case on the basis of the X-ray diffraction pattern of the hydrogenation catalyst, since a change in the structure is accompanied by a significant change in the X-ray diffraction pattern. In general, the content of such oxides other than aluminum oxide is below 50% by weight, preferably below 30% by weight, more preferably below 10% by weight. The degree of purity of the aluminum oxide is preferably higher than 99%.

The production of eggshell catalysts of this kind, including their oxidic supports, is described in WO 2007/107477 A1 (BASF AG), in particular on pages 5 to 10.

Pd/Pt Catalyst:

Preferred transition metal catalysts according to the invention are those that comprise, as active components, one or more metals selected from the group of metals Pd and Pt. Particular preference is given to the metal Pd as the at least one, in particular sole, active component. (Active component=catalytically active component).

Support materials for the catalysts to be used according to the invention are preferably activated carbon or aluminum oxide, more preferably activated carbon.

A catalyst that is particularly preferred in the context of the present invention is Pd on activated carbon (Pd/C).

It is advantageous when the catalysts mentioned have a Pd and/or Pt content from 0.1% to 25% by weight, preferably from 0.5% to 15% by weight, and more preferably from 4% to 11% by weight [in each case based on the reduced metal(s) (oxidation state 0) of the finished catalyst and based on the total weight of the dry catalyst].

Such catalysts are commercially available and obtainable for example under the names Degussa E1002, Degussa E101, Degussa E105, Degussa E106, Engelhard C3630, Eleraeus K201, Heraeus K202, Eleraeus K203, Eleraeus K204, Eleraeus K219.

The catalyst may in particular have a water content in the range from 1% to 150% by weight, more particularly in the range from 3% to 10% by weight (in each case based on the weight of the dry catalyst).

Reaction Procedure:

The following description concerning possible reactors, reaction procedure, reaction conditions, etc. relates to the preparation according to the invention of all possible amines of the formula (1). Unless otherwise stated, the following explanations therefore relate both to amines in which m is 1 and to those in which m is 2 or 3.

Steps 1 and 2 are usually carried out in the liquid phase. The reactants may optionally be diluted with a suitable solvent, such as tetrahydrofuran, dioxane, N-methylpyrrolidone, ethylene glycol dimethyl ether, toluene or xylene. In step 1, alcohols (for example methanol or isopropanol) may also be used. Depending on the chosen reaction conditions, a certain proportion of the reactants and of the solvent will be in the gaseous state in accordance with their partial pressure.

The process of the invention can be carried out either continuously or batchwise.

Examples of suitable reactors for steps 1 and 2 are autoclaves, stirred-tank reactors or fixed-bed reactors, for example shell-and-tube or shaft reactors (shaft reactors being the preferred type of fixed-bed reactor).

Step 1:

The reaction product formed in step 1 according to the invention is normally an imine or Schiff base.

In step 1, the reaction product formed from the reaction of the amino alcohol with the carbonyl compound may be hydrogenated to the intermediate in situ (in-situ reaction procedure). The amino alcohol and the carbonyl compound are here reacted in the presence of hydrogen ($H_2$) and the heterogeneous hydrogenation catalyst. It is likewise possible to first react the amino alcohol and the carbonyl compound and then to hydrogenate the resulting reaction product (optionally after further purification) in accordance with the invention. The reaction of amino alcohol and carbonyl compound does not take place here in the presence of hydrogen ($H_2$) and heterogeneous hydrogenation catalyst.

In an in-situ reaction procedure, the reaction temperature in step 1 is preferably 20 to 250° C., more preferably 40 to 200° C., particularly preferably 60 to 180° C. Step 1 of the process of the invention is preferably carried out at an absolute pressure (=reaction pressure) of 10 to 200 bar, more preferably 30 to 150 bar, and particularly preferably at 50 to 120 bar. The reaction pressure is made up of the partial pressures of all reactants, any solvents present, products, any by-products, and other contaminants.

If the reaction is not carried out in situ, the reaction of amino alcohol and carbonyl compound to the reaction product according to the invention preferably takes place at a temperature of 0 to 250° C. The absolute pressure is preferably 1 to 200 bar. What was said above about the partial pressures applies accordingly. The reaction of the reaction product according to the invention to the intermediate is preferably carried out in the range for pressure and temperature mentioned above for the in-situ reaction procedure.

Step 1 is preferably operated with complete conversion. This means that the conversion based on the amino alcohol or the carbonyl compound, depending on which of these compounds is in deficit, is approximately 100%. In particular, the conversion is 70 to 95%, 80 to 98%, or even 90 to 100%. The compound present in deficit is the one that theoretically may undergo complete conversion (preference is given to using the amino alcohol in excess and the carbonyl compound in deficit; see below). The conversion may be determined for example by taking a small amount of sample from the reactor and analyzing its composition, for example by gas chromatography. The conversion (Conv) is calculated according to the following formula:

$$Conv = 1 - \frac{n}{n_0} * 100\%$$

where n=molar amount of the unreacted amino alcohol/carbonyl compound $n_0$=molar amount of the amino alcohol/carbonyl compound originally used The amino alcohol of the formula (2) is used in an amount that is preferably 0.8 to 1.9 times, more preferably 0.9 to 1.5 times, and particularly preferably 1.1 to 1.3 times, or even 1.1 times to 1.2 times, the molar amount based on the molar amount of the carbonyl groups in the carbonyl compound of the formula (3).

A particular advantage is gained when the amino alcohol is used in a slight excess according to the abovementioned ranges (a maximum of 1.9 times the molar amount). It is then not necessary to separate the amino alcohol from the crude intermediate, since it does not interfere in step 2. The excess amino alcohol may be removed by distillation after carrying out step 2. The amino alcohol thus removed may optionally be reused in step 1 (for example by recycling in a continuous process). Because the amino alcohol is used only in a slight excess, energy and equipment costs are low. If only small amounts of the amine are produced, the amino alcohol cannot be freely recycled in step 1, but must instead be disposed of (e.g. by incineration). This represents an improvement over the prior art, in which 1,2-EDA or 1,2-PDA are normally used in a greater excess than 1.9 times, because the ratio of reactant to be disposed of to product produced is lower in the process of the invention. The smaller the excess of the amino alcohol used, the greater this effect. In this respect, the process of the invention in this embodiment is particularly suitable for preparing smaller amounts of the amines according to the invention. The process of the invention is accordingly preferably operated batchwise. It may also be operated continuously, with steps 1 and 2 each carried out in fixed-bed reactors (identical or different).

The hydrogen ($H_2$) is used in an amount that is preferably 1 to 10 times, more preferably 2 to 5 times, and particularly preferably 3 to 4 times, the molar amount based on the molar amount of the carbonyl groups in the carbonyl compound of the formula (3).

Step 1 may be carried out in an autoclave or a stirred-tank reactor. These reactors are particularly suitable for batch operation. With a stirred-tank reactor, semi-batch operation (feeding in a reactant or a reactant solution) is also possible.

In batch operation, the reactor (e.g. an autoclave or stirred-tank reactor) is usually initially charged with the amino alcohol and the carbonyl compound and the heterogeneous hydrogenation catalyst (catalyst), preferably in the form of a suspension catalyst. The desired reaction pressure may be set for example by pressurizing with hydrogen ($H_2$). It is likewise possible for the amino alcohol and the carbonyl compound to be reacted together in a suitable reactor and the resulting reaction product (optionally after further workup) then reacted in the presence of hydrogen ($H_2$) and the heterogeneous hydrogenation catalyst in the same reactor or in a different one.

In semi-batch operation, the stirred-tank reactor is initially charged with the amino alcohol and the catalyst, preferably in the form of a suspension catalyst, and the reactor is then pressurized with hydrogen until the desired reaction pressure has been set. The carbonyl compound is then added at the reaction temperature and reaction pressure. The addition may be in portions or continuous. The addition is continued until the desired conversion (see above) is reached. It is likewise possible to add the amino alcohol to the initially charged carbonyl compound. In this case, the hydrogenation of the reaction product of the reaction of amino alcohol and carbonyl compound takes place in situ.

It is also possible for the amino alcohol and the carbonyl compound to be reacted in a suitable reactor (with either the amino alcohol or the carbonyl compound initially charged and the other compound added to this) and then the resulting reaction product (optionally after further workup) hydrogenated in the presence of hydrogen ($H_2$) and the heterogeneous hydrogenation catalyst in the same reactor or in a different one.

In batch and semi-batch operation, it is advantageous when the chosen catalyst is used in an amount such that the amount of catalyst (calculated anhydrous), based on the employed amount of amino alcohol of the formula (2), is within the range from 0.1% to 30.0% by weight, in particular within the range from 1.0% to 15.0% by weight.

With the continuous reaction procedure, a fixed-bed reactor (see above) is usually used. The hydrogenation of the reaction product resulting from the reaction of amino alcohol and the carbonyl compound takes place in situ here as described above. Here, the catalyst space velocity is usually 0.01 to 2, in particular 0.1 to 1, kg of carbonyl compound of the formula $(3)/(l_{cat} \cdot h)$, ($l_{cat}$=catalyst volume). Such a procedure may be operated with or without recycling. If recycling is carried out, part of the product stream exiting the reactor is recycled back into the reactor. The recycled product stream is usually cooled in order to achieve a more homogeneous temperature profile across the length of the reactor.

With a continuous reaction procedure, gaseous reactants (in particular hydrogen ($H_2$)) may be circulated. The flow rate of the circulating gas is preferably within the range from 40 to 1500 $m^3$ (at operating pressure)/[$m^3$ of catalyst (bed volume)·h], in particular within the range from 100 to 700 $m^3$ (at operating pressure)/[$m^3$ of catalyst (bed volume)·h]. The circulating gas comprises preferably at least 10%, particularly 50% to 100%, more particularly 80% to 100%, by volume of hydrogen ($H_2$).

The choice of an appropriate reactor and of the reaction procedure essentially depends on the desired amount of the amine to be produced. If this amount is relatively small, the use of an autoclave or stirred-tank reactor in batch operation is preferred. If larger amounts (e.g. several tons) of the amine are to be produced, semi-batch operation or even the continuous reaction procedure is advantageous.

The water of reaction formed in step 1 may be removed from the crude intermediate formed.

Step 2:

In contrast to step 1, in step 2 the reaction of the intermediate with the amine component takes place by definition in the presence of hydrogen and an appropriate catalyst.

The reaction temperature in step 2 is preferably 150 to 250° C., more preferably 170 to 230° C., and particularly preferably 180 to 220° C. Step 2 of the process of the invention is preferably carried out at an absolute pressure (=reaction pressure) of 50 to 250 bar, more preferably 70 to 220 bar, and particularly preferably at 100 to 200 bar. The reaction pressure is made up of the partial pressures of all reactants, any solvents present, products, any byproducts, and other contaminants.

The amine component of the formula (5) is used in an amount that is preferably 1.5 to 100 times, more preferably 1.5 to 30 times, and particularly preferably 2 to 25 times, or even 2.5 to 20 times, the molar amount based on the molar amount of the alcohol groups in the intermediate of the formula (4).

The hydrogen ($H_2$) is used in an amount that is preferably 0.1 to 10 times, more preferably 1 to 5 times, and particularly preferably 2 to 4 times, the molar amount based on the molar amount of the alcohol groups in the intermediate of the formula (4).

Conversion of about 95% of the intermediate obtained in step 1 is usually possible. The conversion based on the intermediate is preferably 20 to 100%, more preferably 50 to 97%, and particularly preferably 70 to 95%. The conversion (Conv) is calculated according to the following formula:

$$Conv = 1 - \frac{n}{n_0} * 100\%$$

where n=molar amount of the unreacted intermediate
$n_0$=molar amount of the intermediate originally used Just as in step 1, the choice of the reactor and of the reaction procedure essentially depend on the desired amount of the amine of the formula (1) to be produced.

When the intermediate has been produced in a batch operation, the further reaction thereof in step 1 is usually likewise carried out in a batch operation. The intermediate formed in step 1 may remain in the reactor (e.g. a stirred-tank reactor) and then undergo reaction (in the same stirred-tank reactor) in step 2.

Step 2 may be carried out e.g. in an autoclave or a stirred-tank reactor. These reactors are particularly suitable for batch operation.

As in step 1, step 2 may also be carried out continuously in a fixed-bed reactor. What was said for step 1 about possible reactors, recycling, circulating gas, and circulating gas amount applies accordingly to step 2.

In batch operation, it is advantageous when the chosen catalyst is used in an amount such that the amount of catalyst (calculated anhydrous), based on the employed amount of intermediate of the formula (4), is within the range from 0.1% to 30.0% by weight, in particular within the range from 1% to 25.0% by weight.

With the continuous reaction procedure in a fixed-bed reactor, the catalyst space velocity is usually 0.01 to 2, in particular 0.3 to 0.6, kg of intermediate compound of the formula (4)/($l_{cat}$·h), ($l_{cat}$=catalyst volume).

With the continuous reaction procedure, steps 1 and 2 may be carried out in different reactors, with
the amino alcohol, hydrogen ($H_2$), and the carbonyl compound fed continuously into a first reactor, where the reaction in step 1 to form the intermediate takes place, and
the intermediate exiting the first reactor, hydrogen ($H_2$), and the amine component are fed continuously into a second reactor, where the reaction in step 2 to form the amine of formula (1) takes place.

It is possible for both reactors to be furnished with the same heterogeneous hydrogenation catalysts or with different ones. The intermediate produced in step 1 is preferably fed through one or more pressure separators (e.g. a high-pressure separator and optionally a medium-pressure separator), but is otherwise fed into the second reactor without further purification and reacted there in step 2. The appropriate reaction conditions for steps 1 and 2 may be chosen as already described above. The same applies to the possible reactors.

In a continuous reaction procedure, steps 1 and 2 are preferably carried out successively in the same reactor on the same heterogeneous hydrogenation catalyst, with
the amino alcohol, hydrogen ($H_2$), and the carbonyl compound fed continuously into a reactor, where the reaction in step 1 to form the intermediate takes place,
the intermediate exiting the reactor is temporarily stored in a suitable container and, once the desired amount of intermediate has been produced,
the intermediate from the container, hydrogen ($H_2$), and the amine component are fed continuously into the reactor, where the reaction in step 2 to form the amine of formula (1) takes place.

Usually, the desired amount of the intermediate of the invention is produced first and stored temporarily in the container (e.g. a tank). The exit stream from the reactor is here usually passed through one or more pressure separators (e.g. a high-pressure separator and optionally a medium-pressure separator). Said intermediate is then passed back into the reactor together with hydrogen and the amine of the formula (4). The appropriate reaction conditions for steps 1 and 2 may be chosen as already described above. The same applies to the possible reactors.

In addition, it is likewise possible to carry out steps 1 and 2 at the same time in the same reactor on the same heterogeneous hydrogenation catalyst. For this, a reactor is initially charged with all the reactants and the reaction carried out there. In this case, the intermediate is formed in situ and converted into the amine of the invention in step 2. It is possible for the reaction to be operated both continuously and batchwise. However, the formation and subsequent reaction of the intermediate in situ, i.e. the performance of steps 1 and 2 one after the other as described above, is not preferable.

The crude amine of the formula (1) produced according to the invention may be further purified. For example, it may be subjected to one or more distillation steps. It is usually possible for excess amine components (e.g. ammonia), any excess amino alcohol, and the water of reaction formed in steps 1 and 2 to be distilled off first. High boilers can be separated through a subsequent distillation step.

It should be pointed out that the process of the invention is not restricted to those embodiments in which exactly one amine of the formula (1) is produced.

The amines of the invention may also be produced simultaneously (i.e. side by side) using the process of the invention, for example by
in step 1, reacting more than one amino alcohol and/or more than one carbonyl compound and then reacting the resulting intermediates with one amine component or optionally a plurality thereof, or
reacting an intermediate obtained in step 1 with more than one amine component in step 2.

For example, a mixture of N-benzyl-1,2-ethanediamine and N-(4-methoxybenzyl)-1,2-ethanediamine can be produced by reacting MEOA with benzaldehyde and 4-methoxybenzaldehyde in step 1 and then reacting the resulting intermediates with ammonia in step 2. Likewise, a mixture of amino alcohols (for example MIPOA and MIPOA') may, for example, be used. Such embodiments have already been described above.

As already stated above, in accordance with the invention amines in which m is 2 or 3 may also be prepared side by side. For example, terephthalaldehyde and 1-4-cyclohexanedicarbaldehyde may together be reacted with MIPOA in step 1 and the resulting intermediates reacted with ammonia in step 2. This results in a mixture of 1,4-bis(2-aminopropylaminomethyl)benzene and 1,4-bis(2-aminopropylaminomethyl)cyclohexane, each of which is an amine of the formula (1).

When a plurality of amino alcohols and/or a plurality of amine component is used in the preparation of amines in which m is 2 or 3, the molecular fragments [$R^6R^7NCHR^5CFHR^4NFHCFHR^2$]— in the formula (1) may differ from one another. The same applies to the molecular fragments in the intermediate of the formula (4). If, for example, terephthalaldehyde is simultaneously reacted with MIPOA and MIPOA' and the resulting intermediates are subsequently reacted with ammonia, this results in the formation not only of 1,2-bis(2-aminopropylaminomethyl)benzene and 1,2-bis(1-amino-2-methylethylaminomethyl)benzene, but also 1,2-(2-aminopropylaminomethyl)(2-amino-1-methylethylaminomethyl)benzene. In the latter compound, $R^4$ is hydrogen (H) and $R^5$ methyl in one molecular fragment and in the other molecular fragment $R^4$ is methyl and $R^5$ is hydrogen (H).

The mixtures described in the preceding paragraphs may be used directly, depending on the desired end use. It is likewise possible to separate the respective amines (for example by distillation).

For the avoidance any doubt, it should be pointed out that, in situations in which a plurality of amines of the formula (1) is produced simultaneously, that is to say a plurality of reactants is used, the corresponding preferred, more preferred, and particularly preferred molar ratios mentioned above are based on the sum of the molar amounts of the respective reactants. In particular, this means the following. The amino alcohol(s) of the formula (2) is/are used in the abovementioned molar amounts based on the molar amount of the carbonyl groups in the carbonyl compound(s) of the formula (3). Hydrogen ($H_2$) is used in the abovementioned molar amounts based on the molar amount of the carbonyl groups in the carbonyl compound(s) of the formula (3). The amine component(s) of the formula (5) is/are used in the abovementioned molar amounts based on the molar amount of the alcohol groups in the intermediate(s) of the formula (4). Hydrogen ($H_2$) is preferably used in the abovementioned molar amounts based on the molar amount of the alcohol groups in the intermediate(s) of the formula (4).

For example, if 0.5 mol of benzaldehyde and 0.5 mol of 2-methylbenzaldehyde are reacted with 1.3 times the molar amount of MIPOA and MIPOA' (molar ratio 19:1), this means that 1.235 mol of MIPOA and 0.065 mol of MIPOA' must be used.

The examples that follow serve to elucidate the invention without restricting it in any way.

EXAMPLES

Gas chromatography (for inventive examples): RTX5 Amine column, length 30 m, diameter 0.32 mm, film thickness 1.5 µm. Temperature program: 60° C. start temperature, with 4° C./min to 280° C., hold for 15 min.

Inventive:

Step 1:

A glass flask with nitrogen blanketing, thermometer, and a reflux condenser was charged with 82.6 g (1.1 mol) of monoisopropanolamine (MIPOA and MIPOA' in a molar ratio of 95:5, hereinafter referred to collectively as "monoisopropanolamine"), the flask was immersed in an ice bath, and benzaldehyde (106.1 g, 1.0 mol) was then added dropwise over a period of 30 minutes. The mixture became warm as a result of the heat of reaction evolved. On cessation of the heat of reaction, the mixture of Schiff base and excess monoisopropanolamine solidified. To this was then added sufficient THF that the mixture formed a clear solution at 35° C. The entire reaction mixture was divided between four high-pressure autoclaves, each with a capacity of 160 ml and equipped with a pitched-blade stirrer, a catalyst cage, a hydrogen inlet, and a thermocouple. Each autoclave was fitted with electric heating. Each catalyst cage was filled with 6 g of a Pd/Ag catalyst on aluminum oxide support (0.3% Pd, 0.1% Ag, extrudates, diameter 2.8 mm in accordance with WO 2007/107477 A1 (BASF AG), example on page 19 f.). The autoclaves were closed and inertized, pressurized with 20 bar of hydrogen, and the contents then heated to 100° C. On reaching the reaction temperature, the hydrogen pressure was increased to 80 bar and the contents were stirred for 12 h. Hydrogen consumed was replenished. A sample was analyzed by gas chromatography. The analysis result with retention time, assignment, and GC area % values is shown in Table 1. THF is subtracted. The THF concentration was approximately 63%. Assignment was by gas chromatography with coupled mass spectrometry (GC-MS). Selectivity in respect of N-benzyl-monoisopropanolamine (N-benzyl-MIPOA and N-benzyl-MIPOA') was 95.6%.

TABLE 1

| Analysis results for the benzylation of monoisopropanolamine | | | | | | | |
|---|---|---|---|---|---|---|---|
| Retention time | 6.13 | 6.32 | 7.63 | 14.88 | 26.09 | 26.38 | |
| Compound | Monoisopropanolamine | Unidentified | Toluene | Benzylamine | N-Benzyl-MIPOA | N-Benzyl-MIPOA' | Total of others |
| GC area % | 2.19 | 0.49 | 1.00 | 0.04 | 91.55 | 4.02 | 0.71 |

Step 2:

To the mixture obtained was added triethylene glycol dimethyl ether (TEGDME) to permit evaluation of the formation of volatile compounds or high boilers in the subsequent reaction. A GC of the reaction mixture used contained 7.5% of TEGDME (GC area %). 50 g of the mixture (approx. 0.19 mol of N-benzyl-monoisopropanolamine) was then transferred to a 0.3 L high-pressure autoclave equipped with a disc-type gassing stirrer, thermocouple, electric heating, hydrogen inlet, and liquid inlet for ammonia, into which had previously been introduced 10 g of a reduced-passivated amination catalyst (comprising Ni, Co, Cu, Sn on $Al_2O_3$ and obtained according to WO 2011/

067199 A1 (BASF AG), example 5) in a catalyst cage. 65 g (3.8 mol) of ammonia was then added, corresponding to a molar ratio of about 20:1. The autoclave was then pressurized at room temperature with 30 bar of H₂ and heated to 180° C. with stirring. On reaching this temperature, the pressure was increased to 200 bar by repressurization with hydrogen. Once the pressure had fallen to 190 bar, the autoclave was repressurized to 200 bar with hydrogen (consumption of hydrogen due to reduction of the catalyst). Stirring was then continued for 10 hours under these conditions. The reaction mixture was then filtered to remove the catalyst.

The mixture was analyzed by gas chromatography using the same method as stated above. THF and TEGDME were subtracted. TEGDME was detected in a content of 7.5%, corresponding to the relative amount in the reactant mixture. Form this, it was concluded that neither volatile by-products nor high boilers that do not pass through the GO were formed.

The results are shown in Table 2.

TABLE 2

| Analysis results for the amination of N-benzyl-monoisopropanolamine | | | | | | | |
|---|---|---|---|---|---|---|---|
| Retention time | 6.13 | 7.63 | 14.88 | 25.88 | 26.09 | 26.19 | 26.38 |
| Compound | 1,2-PDA | Toluene | Benzylamine | $N^1$-Benzyl-PDA | N-Benzyl-MIPOA | $N^2$-Benzyl-PDA | N-Benzyl-MIPOA' | Total of others |
| GC area % | 5.8 | 1.2 | 9.3 | 72.6 | 4.4 | 2.0 | 2.0 | 2.7 |

In the calculation of selectivity, GC area % is equated to % by weight.

The molar conversion of N-benzyl-monoisopropanolamine was 93%, the selectivity for the sum of the two isomers $N^1$-benzyl-PDA and $N^2$-benzyl-PDA of the target product N-benzylpropanediamine (N-benzyl-PDA) was 78%. 1,2-Propanediamine and benzylamine were formed as further products of value. Taking into account the molar masses of the identified products formed from benzaldehyde, the molar selectivity for the conversion of benzaldehyde to N-benzyl-PDA ($N^1$-Benzylpropanediamine and $N^2$-benzylpropanediamine) was 77%. Taking into account the partial conversion of the N-benzyl-monoisopropanolamine (intermediate) into N-benzyl-PDA, the selectivity was in fact 83%.

Comparative Example (Non-Inventive)

6.2 g (0.08 mol) of 1,2-propylenediamine (1,2-PDA) and 35.6 g of isopropanol were placed in a glass flask equipped with a reflux condenser with nitrogen blanketing, thermometer, and stirrer and 8.9 g (0.08 mol) of benzaldehyde was added to this dropwise. The contents were stirred for 2 h and then transferred to an autoclave containing a catalyst cage filled with 20 ml (10.7 g) of the palladium catalyst described above (according to WO 2007/107477 A1 (BASF AG), example on page 19 f). The autoclave was pressurized at room temperature with 20 bar of H₂ and stirred. The mixture was then heated to 90° C. and, on reaching this temperature, the hydrogen pressure was increased to 90 bar and stirring was continued for 4 h under these conditions. The hydrogen pressure was kept broadly constant by repressurizing to compensate for hydrogen consumed. A sample was then analyzed by gas chromatography. The method was as follows: column DB1, length 30 m, diameter 0.32 mm; layer thickness 3 μm; temperature program 80° C. start temperature, 10° C./min to 280° C., hold at 280° C. for 50 min.

The analysis result with retention times, assignments, and GC area % values is shown in Table 3. Isopropanol is subtracted.

TABLE 3

| Analysis results for the reductive amination of benzaldehyde with 1,2-PDA | | | | | | |
|---|---|---|---|---|---|---|
| Retention time | 5.85 | 7.18 | 18.76 | 18.97 | 26.19 | |
| Compound | 1,2-PDA | Toluene | $N^1$-Benzyl-PDA | $N^2$-Benzyl-PDA | N,N'-Dibenzyl-PDA | Total of others |
| GC area % | 9.49 | 4.94 | 20.17 | 9.96 | 53.12 | 2.3 |

The conversion was 100% for benzaldehyde and 90.5% for 1,2-PDA. Taking the molar masses into account permits the selectivity for the conversion of benzaldehyde to N-benzylpropanediamine to be calculated. This was 25%.

Discussion of the Results:

The examples show that the selectivity that can be achieved with the process of the invention (selectivity of 77%) is considerably higher than that achieved through the amination of benzaldehyde with 1,2-PDA (selectivity of 25%). A particular surprise for those skilled in the art is that no appreciable formation of toluene occurred in step 2. Those skilled in the art will know that in organic chemistry a benzyl group is used as a so-called protecting group for an amino group. This means that the benzyl group, in its function as a protecting group, prevents the amino group from undergoing any undesired reaction during a complicated, multistep chemical synthesis. At the end of the synthesis, the protecting group is cleaved off again. This is usually done under the reaction conditions of step 2 and using the employed heterogeneous hydrogenation catalysts. Those skilled in the art would have accordingly expected the formation of toluene in step 2, i.e. the deprotection again of the amino group, to occur to such a considerable degree that N-benzylpropanediamine would be formed only in very small amounts.

The invention claimed is:
1. A process for preparing amines of the formula (1),

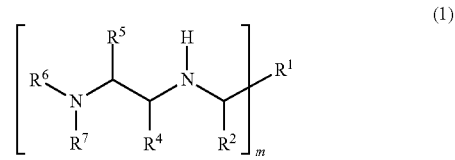

in which
m is 1, 2 or 3, wherein
when m is 1
    $R^1$ is an aliphatic $C_{1-60}$ hydrocarbon radical or $C_{4-60}$ hydrocarbon radical that contains at least one cycloaliphatic or aromatic ring, said $C_{1-60}$ or $C_{4-60}$ hydrocarbon radical optionally containing one or more heteroatoms independently selected from the group consisting of nitrogen (N), oxygen (O), and sulfur (S), and $R^2$ is hydrogen (H), C1-6 alkyl or phenyl, or $R^1$, $R^2$ together are $-(CH_2)_j-Y-(CH_2)_k-$, where Y is methylene, oxygen (O), sulfur (S), or $NR^3$ (where $R^3$ is $C_{1-4}$ alkyl) and j and k are independently an integer from 1 to 4, when m is 2 or 3

$R^1$ is a di- or trivalent $C_{4-20}$ hydrocarbon radical that contains at least one cycloaliphatic or aromatic ring, said hydrocarbon radical optionally containing one or more heteroatoms independently selected from the group consisting of nitrogen (N), oxygen (O), and sulfur (S), and $R^2$ is hydrogen (H), $C_{1-6}$ alkyl or phenyl, and $R^4$ and $R^5$ are independently hydrogen (H) or $C_{1-16}$ alkyl, $R^6$ and $R^7$ are independently hydrogen (H) or $C_{1-4}$ alkyl, comprising the steps of A. reacting an amino alcohol of the formula (2)

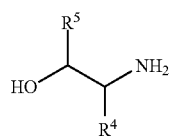

(2)

with a carbonyl compound of the formula (3)

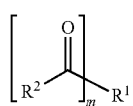

(3)

and subsequent hydrogenation of the resulting reaction product with hydrogen ($H_2$) on a heterogeneous hydrogenation catalyst to form an intermediate of the formula (4)

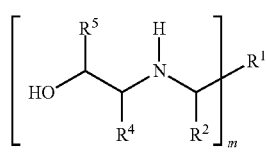

(4)

B. reacting the intermediate obtained in step 1 with an amine component of the formula (5)

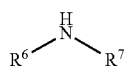

(5)

in the presence of hydrogen ($H_2$) and a heterogeneous hydrogenation catalyst to form a corresponding amine of the formula (1), where m and the radicals R', $R^2$, $R^4$, $R^5$, $R^6$, and $R^7$ in the formulas (2) to (5) are as defined in formula (1).

2. The process according to claim 1, characterized in that, in step A, the amino alcohol of the formula (2) is used in an amount that is 0.8 to 1.9 times the molar amount based on the molar amount of the carbonyl groups in the carbonyl compound of the formula (3).

3. The process according to claim 1, characterized in that, in step B, the amine component of the formula (5) is used in an amount that is 1.5 to 100 times the amount based on the molar amount of the alcohol groups in the intermediate of the formula (4).

4. The process according to claim 1, for preparing amines of the formula (1) in which m is 2, where $R^1$ is an optionally substituted phenylene, cyclohexylene, dicycloheptylene, tricyclododecylene, pentacyclopentadecylene, furandiyl, tetrahydrofurandiyl, thiophenediyl, tetrahydrothiophenediyl, or N,N'-piperazine-bis(2,2-dimethylpropane)diyl radical, and $R^2$ is hydrogen ($H_2$), methyl or phenyl.

5. The process according to claim 1 for preparing amines of the formula (1) in which m is 1, where $R^1$ is $C_{3-50}$ alkyl, $C_{3-50}$ alkoxyalkyl, $C_{4-12}$ cycloalkyl, $C_{4-30}$ alkoxycycloalkyl, $C_{4-30}$ alkylcycloalkyl, or radical of the formula (A), (B) or (C),

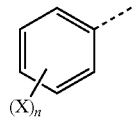

(A)

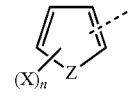

(B)

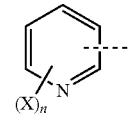

(C)

where, in formulas (A), (B), and (C)

X are identical or different radicals selected from the group consisting of $C_{1-18}$ alkyl, $C_{1-18}$ alkoxy, and $C_{1-18}$ dialkylamino, Z is oxygen (O), sulfur (S) or $NR^9$ (where $R^9$ is $C_{1-4}$ alkyl), n is an integer from 0 to 3, and $R^2$ is hydrogen (H), methyl, ethyl or phenyl, or $R^1$ and $R^2$ together are $-(CH_2)_j-Y-(CH_2)_k-$, where Y is methylene or oxygen (O) and j and k are independently an integer from 1 to 2.

6. The process according to claim 1 for preparing amines of the formula (1) in which m is 1, where
$R^1$ and $R^2$ are both methyl or both phenyl, $R^1$ is 3-methylbutyl and $R^2$ is methyl, or $R^1$ is n-pentyl and $R^2$ is ethyl,
or
$R^1$ is selected from the group consisting of i-propyl, phenyl, 2-methylphenyl, 3-methylphenyl, 4-methylphenyl, 2,5-dimethylphenyl, 4-ethylphenyl, 4-isopropylphenyl, 4-tert-butylphenyl, 2-methoxyphenyl, 3-methoxyphenyl, 4-methoxyphenyl, 2,3-dimethoxyphenyl, 2,4-dimethoxyphenyl, 2,5-dimethoxyphenyl, 3,4-dimethoxyphenyl, 3,5-dimethoxyphenyl, 2,4,5-trimethylphenyl, 2,4,6-trimethylphenyl, 2,4,5-trimethoxyphenyl, 2,4,6-trimethoxyphenyl, 3,4,5-trimethoxyphenyl, 2-dimethylaminophenyl, 3-dimethylaminophenyl, 4-dimethylaminophenyl, 2-furyl, and 3-furyl, and
$R^2$ is hydrogen (H) or methyl;
or
$R^1$ and $R^2$ are together n-pentylene.

7. The process according to claim 1 for preparing amines of the formula (1) in which m is 1, where $R^1$ is phenyl, and $R^2$ is hydrogen.

8. The process according to claim 1, characterized in that $R^6$ and $R^7$ are hydrogen (H).

9. The process according to claim 1, characterized in that $R^4$ or $R^5$ is methyl and the other radical is in each case hydrogen (H) or in that $R^4$ and $R^5$ are both hydrogen (H).

10. The process according to claim 1 for preparing amines of the formula (1) in which m is 1 and in which $R^4$ is hydrogen (H) and $R^5$ is methyl (formula (1.1)) or $R^4$ is methyl and $R^5$ is hydrogen (H) (formula (1.2))

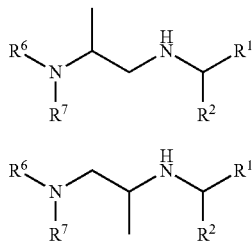

(1.1)

(1.2)

where
in step A, 1-aminopropan-2-ol (MIPOA) and 2-aminopropan-1-ol (MIPOA') are reacted with a carbonyl compound of the formula (3) to form the respective intermediates of the formulas (4.1) and (4.2),

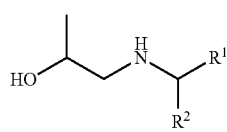

(4.1)

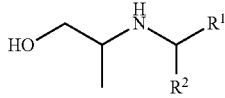

(4.2)

in step B, the intermediates obtained in step A are reacted with an amine component of the formula (5) to form the corresponding amines of the formulas (1.1) and (1.2).

11. The process according to claim 10 for preparing $N^1$-benzyl-1,2-propylenediamine and $N^2$-benzyl-1,2-propylenediamine in which 1-aminopropan-2-ol (MIPOA) and 2-aminopropan-1-ol (MIPOA') are reacted with benzaldehyde in step A and the resulting intermediates (N-benzyl-1-aminopropan-2-ol and N-benzyl-2-aminopropan-1-ol) are reacted with ammonia in step B.

12. The process according to claim 10, characterized in that 1-aminopropan-2-ol (MIPOA) and 2-aminopropan-1-ol (MIPOA') are used in a molar ratio of MIPOA to MIPOA' of 15:1 to 23:1.

13. The process according to claim 1, characterized in that the heterogeneous hydrogenation catalyst used in steps A and B is a catalyst comprising one or more metals from group VIII B and/or group IB of the periodic table of the elements.

14. The process according to claim 13, characterized in that the catalyst has a support material.

15. The process according to claim 13, characterized in that the heterogeneous hydrogenation catalyst used is a catalyst that comprises Cu and/or Ni and/or Co.

16. The process according to claim 15, characterized in that the heterogeneous hydrogenation catalyst used is a supported catalyst comprising copper, nickel, and cobalt in which the catalytically active mass of the catalyst, prior to the reduction thereof with hydrogen, comprises oxygen-containing compounds of aluminum, copper, nickel, and cobalt and from 0.2% to 0.5% by weight of oxygen-containing compounds of tin, calculated as SnO.

17. The process according to claim 13, characterized in that
in step A
a heterogeneous hydrogenation catalyst that is an eggshell catalyst is used, which comprises at least one metal from group VIIIB of the periodic table of the elements as the hydrogenation metal and additionally a promoter on an oxidic support, at least 80% of the metal from group VIIIB of the periodic table of the elements being present in a layer between the surface of the catalyst and a penetration depth corresponding to not more than 80% of the radius of the catalyst, calculated from the surface of the catalyst,
or
a heterogeneous hydrogenation catalyst that is a supported catalyst is used, which comprises Pd and/or Pt as the catalytically active metal and has activated carbon or aluminum oxide as support,
in step B a catalyst according to claim 13 is used.

* * * * *